United States Patent [19]

Fukui et al.

[11] 4,043,945

[45] Aug. 23, 1977

[54] METHOD OF PRODUCING THIN LAYER METHANATION REACTION CATALYST

[75] Inventors: Yutaka Fukui; Fumio Hataya; Ryoichi Sasaki; Fumito Nakajima; Shimpei Matsuda; Munehiko Tonami; Ryo Hiraga, all of Hitachi, Japan

[73] Assignee: Hitachi, Ltd., Japan

[21] Appl. No.: 630,881

[22] Filed: Nov. 11, 1975

[30] Foreign Application Priority Data

Nov. 11, 1974  Japan .................................. 49-128993

[51] Int. Cl.² .......................... B01J 21/04; B01J 23/74
[52] U.S. Cl. ............................ 252/466 J; 252/477 Q; 427/253; 427/438
[58] Field of Search ...................... 252/477 Q, 466 J; 427/253, 438; 148/6

[56] References Cited

U.S. PATENT DOCUMENTS

| | | | |
|---|---|---|---|
| 2,532,283 | 11/1950 | Brenner et al. | 427/438 |
| 3,716,398 | 2/1973 | Stueber et al. | 427/253 |
| 3,846,344 | 11/1974 | Larson et al. | 252/477 Q |

*Primary Examiner*—W. J. Shine
*Attorney, Agent, or Firm*—Craig & Antonelli

[57] ABSTRACT

A catalyst layer is formed on the metallic surface of a structure constructing a reactor by diffusing a developable metal into the structure by the pack cementation method and developing the diffused metal. The catalyst layer is metallurgically combined with the structure, so that it has excellent mechanical strength and heat conductivity. Thus, by using the structure having the catalyst layer as a heat exchanger type methanation reactor it is possible to obtain a methanation reactor enabling an extremely enhanced rate of reaction to be obtained with superior operability and at great savings.

12 Claims, 3 Drawing Figures

DIFFUSION LAYER    BASE METAL    (x200)

METHOD OF PRODUCING THIN LAYER METHANATION REACTION CATALYST

BACKGROUND OF THE INVENTION

1. Field of the Invention

This invention relates to a method of producing a Raney type thin layer catalyst metallurgically combined with the surface of a structure.

2. Description of the Prior Art

Raney catalysts find extensive applications as catalyst for hydration reactions of ethylenic linkage and methanation reaction. The Raney catalyst is manufactured by forming an alloy of a catalytic metal such as nickel, cobalt, chromium and iron and an active metal such as aluminum, magnesium and silicon and then dissolving the active metal by means of an acid or alkali solution. The most common Raney catalyst is manufactured by pulverizing nickel-aluminum alloy with a nickel content of 30 to 50 weight percent into powder of a grain size of 150 to 200 mesh and immersing the powder in a caustic soda solution of 3 normal concentration at 50° C for developing aluminum.

This catalyst is in the form of porous particles having dimensions on the order of atomic size. In use, it is charged in a reactor and provides catalytic activity for the reaction gas passing through the charged layer.

The most typical methanation reaction is one represented by $CO + 3H_2 \rightarrow CH_4 + H_2O - \Delta H = 49$ kcal/mol. Since this reaction is an exothermic reaction, the heat of reaction has to be removed to control the temperature. Also, since the volume of the product system is one half that of the reaction material system, the pressure has to be increased to increase the reaction speed. Accordingly, the ordinary methanation reaction is carried out under high temperature high pressure conditions of 300° to 600° C and 20 to 70 atm.

Where the afore-mentioned powder layer is used as the catalyst, the removal of heat is very difficult. Accordingly, a dilution method is adopted as a means for repressing the rise of temperature due to reaction heat. The dilution method is one in which part of the product gas is fed back to the material gas to thereby dilute the material gas. Increasing the partial pressure of methane in the gaseous phase reaction system a simultaneous leads to increase in the heat capacity of the gaseous phase and to a slippage in the balance of reaction, thus restricting the production of methane and therefore preventing a sudden temperature rise due to the reaction heat. However, in order to restrict the reaction by this method about 90 percent of the product gas has to be recirculated, thus leading to a reduced yield and also to an extreme increase in the size of the reactor system.

It has been proposed to carry out the methanation reaction by using a heat exchanger type reactor having the same construction as a heat exchange with a view to maintaining a low reaction temperature for increasing the rate of conversion into methane by directly removing the heat of reaction from the reaction system. For example, this method resorts to a catalyst which is constituted by the reactor tube wall.

Heretofore, the tubular catalyst consisting of Raney nickel has been formed by coating powdery nickel-aluminum alloy by sprayed metal coating over the outer surface of a tube of a different material and subsequently developing aluminum through treatment with alkali.

Since the methanation reaction is a high temperature and high pressure reaction, however, a methanation reactor using as tubular catalyst a reactor tube provided with a catalyst layer formed on the outer surface of the tube is disadvantageous in that the whole apparatus accommodating the reactor tube, the outer surface of which is exposed to high temperature and high pressure, must have a temperature-resistant pressure-bearing structure so that the cost of the apparatus is high. In addition, since the methanation reaction is an exothermic reaction producing a great deal of heat, the reaction heat has to be removed as efficiently as possible. However, in the prior art construction where the reactor tube has a catalyst layer on its outer surface and is cooled on its inner, the reaction area is greater than the cooling area and sufficient heat exchange therefore cannot be obtained.

Further, in the sprayed metal coating of a high aluminum alloy such as Raney nickel, preferential oxidation aluminum having a greater capability of oxidation takes place to result in the formation of aluminum oxide at the alloy surface. Thus, the peel-off resistance of the sprayed metal coating layer is extremely low, that is, the catalyst layer formed on the outer surface of the tube by the sprayed metal coating method is very likely to peel off.

If the catalyst layer is formed on the inner surface of the tube, the cooling efficiency and peel-off resistance can be increased compared to the case of an outer surface catalyst layer. However, it is very difficult to form a sprayed metal coating layer on the inner surface of a tube of a diameter less than 50 millimeters with a sprayed metal coating torch because of the shape thereof. In cases where it is possible, manufacturing costs are high.

In the meantime, it has been proposed to form a catalyst layer on the inner surface of a tube by coating the inner surface with a developable metal by means of electroplating, vapor depositions or immersion in the molten metal, subsequently diffusing the developable metal into the catalytic metal through heat treatment and then developing the catalyst layer. By this method, however, a uniform catalyst layer cannot be obtained unless a residual layer of non-diffused developable metal is removed prior to the development, and the removing operation is very troublesome. Further, failure of diffusion is likely to result depending upon the state of boundary between the catalytic metal layer and developable metal layer. Thus, it is very difficult to form a uniform catalyst layer on the inner surface of a tube of long length.

Summary of the Invention:

A first object of the invention is to provide a method of manufacture of a catalyst structure carrying a thin Raney catalyst layer of excellent heat conductivity.

A second object of the invention is to provide a methanation reactor using a reactor tube, the surface of which is constituted by the Raney catalyst.

A third object of the invention is to provide the production method of a composite catalyst, which consists of a base material in the form of a small diameter tube having sufficient mechanical strength, and in which a catalyst layer is formed on the inner surface of the tube in metallurgically closely combined relation to the base material.

DESCRIPTION OF PREFERRED EMBODIMENTS

Figure 1:
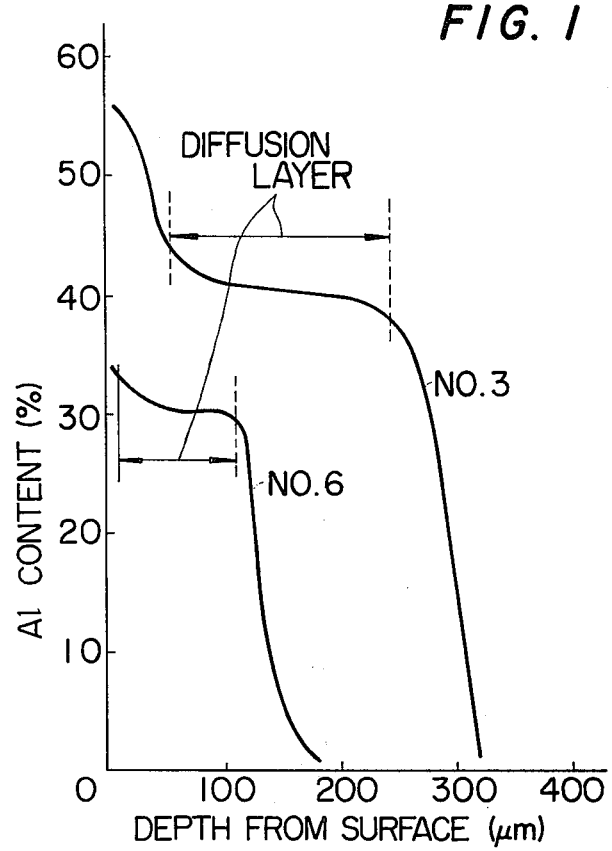
FIG. 1 is a graph showing the depth-wise distribution of the concentration of aluminum diffused in base material, with No. 3 and No. 6 indicating the number of samples.

The method of manufacture of Raney catalysts according to the invention comprises the steps of diffusing a developable metal into a surface portion of a metal capable of conversion into a catalyst by the pack cementation method and then developing the diffused metal through treatment with alkali or acid.

Since a metal capable of development is diffused into a surface portion of a metal to be converted into a catalyst by the pack cementation method, it is possible to form a uniform catalyst layer, to form a catalyst layer on the inner surface of 3 meters length tube which inner diameter is above 5 millimeters, to freely control the thickness of the catalyst layer and to use an alloy containing a metal capable of conversion into a catalyst as substrate for converting a surface portion thereof into the catalyst.

Since the catalyst layer formed in this way is in close metallurgical contact with the base metal, heat can be readily removed from it through the base so that it is possible to design a methanation reactor having high cooling rate. This means that it is possible to design reactors of various types meeting specific purposes, for instance in which reaction gas and cooling medium are passed on the respective inner and outer surfaces of the tube, and in which reaction stages and cooling stages are alternately laminated.

For the reaction process the conventional re-circulation system or one-pass system may be adopted, and the most economical system may be selected depending upon the scale of the process and the present conditions of the reaction.

The base metal for the thin layer catalyst according to the invention contains at least one member of a group consisting of nickel, copper, cobalt, manganese, chromium and tin. Among these elements, nickel is superior in catalytic performance. Nickel plates, tubes or wires with purity of 99 percent or higher are preferred from the standpoints of both catalytic activity and processibility. However, they are disadvantageous with respect to tensile strength which is about 45 kg/mm$^2$ at normal temperature but which tends to fall sharply when the temperature exceeds 400° C and which reduces to about 25 kg/mm$^2$ at 500° C. Accordingly, where high mechanical strength at high temperatures is required, nickel-chromium alloys, nickel-copper alloys and nickel-chromium-iron alloys are used. However, with reduction of the nickel content the catalytic activity is correspondingly reduced, and in this sense the nickel content must be at least 30 percent by weight, more preferably at least 50 percent by weight. Incidentally, it is possible to substitute cobalt for a part of the nickel. Also, chromium can be substituted though its activity is lower than nickel. A preferred base material should contain at least 45 percent by weight of nickel, and exhibit a tensile strength of no less than 35 kg/mm$^2$ and a percentage of elongation of no less than 20 percent at 500° C.

Examples of the metal to be developed are aluminum, silicon, zinc and magnesium. Of these elements, aluminum is the most preferred. When it is combined with nickel, catalytic activity is obtained with a nickel-to-aluminum atomic ratio of at least 0.3.

The diffusion of the metal for development into the catalyst substrate metal is carried out by the pack cementation method. The pack cementation is effected by contacting the catalyst substrate metal with a powder mixture of the developable metal, powder of an inactive sintering-proof carrier for the developable metal and powder of an active agent such as ammonium chloride in a non-oxidizing high temperature atmosphere. The pack cementation method has the following advantages:

1. Since the surface of the catalyst substrate metal contacts aluminum in the gaseous form, aluminum can diffuse into the metal even from the surface thereof which is not in perfect contact with the mixture.

2. The thickness and composition of the alloyed layer can be readily controlled by controlling the composition of the mixture, heating temperature and heating period and also through repeated diffusion. Also, thickness of excellent uniformity can be obtained.

3. The superficies of alloyed layer is always smooth.

4. The processibility is superior.

If the grain size of the mixture is 150 mesh or less, it has excellent fluidity and can readily fill small-diameter tubes of about 3 millimeters in inner diameter and equivalently narrow spaces. The heating is effected by placing the system in the closed state within an electric furnace or, in case of a long tube, moving the external heat source from one end to the other end of the tube.

The quantity of the developable metal powder in the pack ranges from 1 to 50 percent by weight, more preferably from 10 to 30 percent by weight. If the quantity of the developable metal powder is insufficient, the content of the developable metal in the diffusion layer is liable to be too low to provide sufficient catalytic activity. On the other hand, if the quantity exceeds 50 percent by weight, it is likely that particles of the developable metal will sinter together to result in incomplete diffusion or will lead to non-reusability of the pack after re-adjustment.

The heating temperature and period of course have bearing upon the thickness and composition of the diffusion layer, so these conditions are previously determined through experimentation.

Regarding the thickness of the diffusion layer, it should be neither too thin nor too thick. If the layer is too thin, catalytic activity will not be obtained. On the other hand, too thick a layer should be avoided because it is likely to peel off due to internal stress and reduces heat conductivity. The active catalyst layer has numerous micropores ranging from several hundred to several thousand Å in diameter. The thickness of the catalyst layer should be at least several times the micropore diameter. In the methanation reaction or the like where gas having comparatively small molecular diameter is treated under high pressure, the catalyst layer should have a considerable thickness since the reaction gas readily reaches to a deep level. With the catalyst according to this invention the adequate thickness is between 1 micron to 500 microns. The depth of diffusion of the developable metal may be determined with 1.2 to 5 times the thickness of the catalyst layer to be formed as a criterion. The thickness of the diffusion layer is determined by the content of the developable metal in the pack, the heating temperature and period. For example, in case of diffusing aluminum into nickel as catalyst substrate metal by using a pack with an aluminum content of 20 weight percent and at a heating temperature of 800° C, a diffusion layer with a thickness of about 10 micron meters is obtained in a heating period of about 10 minutes and a thickness of about 100 micron meters in a heating period of about one hour. Thus, the thickness of the diffusion layer can very readily be controlled to a desired value.

The development of the developable metal is carried out by using an alkaline or acidic aqueous solution or the like suited to the metal to be developed. For example, in case of a nickel-aluminum alloy the development is usually carried out by immersion in an aqueous solution containing 10 to 20 weight percent of caustic soda and at a temperature of 50° to 80° C, followed by washing with water and then with alcohol. After the development, the system is isolated from air. If it is found necessary, the surface of the catalyst layer formed through the development is oxidized to a very slight extent, and immediately before the commencement of the methanation reaction it is activated for use by passing a reducing gas.

In case of rendering the inner surface of the tube active, the solution is injected into the tube from the lower open end thereby by means of a chemical pump, and the liquid overflowing from the upper end of the tube is re-circulated. Since a great quantity of hydrogen gas is produced during the development, a gas separator for separating the produced gas is provided at the overflow end of the tube.

While various types of reactors may be designed in accordance with the invention, the structure that takes fullest advantage of this inventions characteristics is a reactor having a cooler construction with the catalyst layer found on the inner surface of a tube and a cooling medium adapted to flow over the outer surface of the tube. The strength on the side of a shell within which a cooling medium is sealed may be reduced if the mechanical strength of the tube constituting the base of the catalyst layer is sufficient to withstand the pressure at the time of the methanation reaction. The diameter of the tube is preferably as small as possible because the smaller the inner diameter of the tube the higher the pressure bearing resistance of the tube and the greater the ratio of the cooling area to the gas quantity. Of course, the invention may be realized by forming the catalyst layer on the outer side of the tube. As another example of the reactor that may be formed in accordance with the invention, a plurality of plates are used as base instead of a tube, with the plates each formed with a catalyst layer on one side and stacked such that reaction gas and cooling medium are passed through alternate space between adjacent plates. In this case, the non-reaction gas may be used as part of the cooling medium by appropriately arranging the spaces.

Without limiting this invention, the following examples are given to illustrate some preferred modes of the invention.

EXAMPLE 1.

99.8 Percent pure nickel tubes with an outer diameter of 16 millimeters and a length of 1.2 meters were used. Their outer surfaces were polished, and they were washed with water and dried. Then, their opposite open ends were closed with plugs. As the pack cementation apparatus, a sealed steel vessel provided only with an exhausting means, inert gas introducing and exhausting means and a heating means were used. The tube to be treated is placed together with the pack within the sealed vessel. Then, after pressure reduction the temperature was raised while causing inert gas to flow. After a predetermined temperature was attained, the resultant state was maintained for a predetermined period.

Table 1 below shows the composition of the packs used and treating conditions as well as the depth of the diffusion layer and concentration of diffused aluminum by cutting each treated tube and polishing the cut surface.

Table 1

| Sample No. | Pack composition | | | Temp. (° C) | Time (min.) | Diffusion layer | | $CH_4$ content (%) |
|---|---|---|---|---|---|---|---|---|
| | Al | $NH_4$-Cl | $Al_2O_3$ | | | Depth ($\mu m$) | Al concentration (%) | |
| 1 | 60 | 1 | rest | 900 | 120 | 300 | 55 | 40 |
| 2 | 40 | 1 | rest | 900 | 120 | 240 | 50 | 35 |
| 3 | 20 | 1 | rest | 900 | 120 | 180 | 40 | 37 |
| 4 | 20 | 0.5 | rest | 800 | 60 | 45 | 40 | 34 |
| 5 | 20 | 0.5 | rest | 600 | 120 | 25 | 50 | 37 |
| 6 | 5 | 1 | rest | 900 | 120 | 100 | 30 | 30 |
| 7 | 5 | 1 | rest | 1000 | 120 | 150 | 30 | 29 |
| 8 | 1 | 1 | rest | 800 | 120 | 10 | 20 | 2 |

The concentration of aluminum in the diffusion layer was measured with an X-ray microanalyzer.

FIG. 1 shows the distribution of aluminum in samples Nos. 3 and 6.

Figure 2:
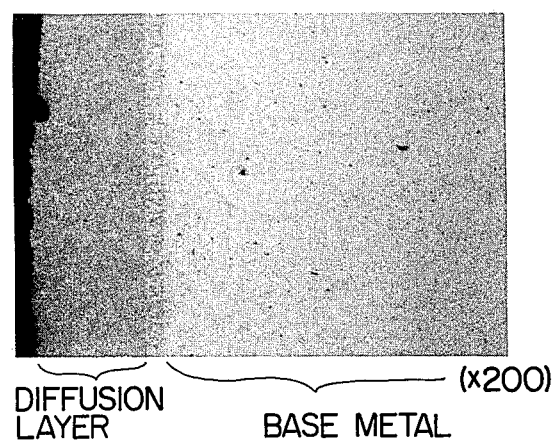
FIG. 2 is a microscopic photograph of a section of the catalyst of sample No. 6.

FIG. 2 is a microscopic photograph of the section of sample No. 6.

It will be seen that the base metal and diffusion layer are clearly distinguished from each other.

In sample No. 1 very shallow microcracks were locally formed at the diffusion layer surface. Although the cracks offered no problems in the instant experiments, they are not preferred over long periods of use. In addition, aluminum powder agglomerates to form a sintered body, so that it is difficult to re-use the pack. With the packs in the other samples, the agglomeration of aluminum was virtually unrecognized.

The developing treatment was carried out by immersion in an aqueous solution containing 20% caustic soda and at a temperature of 50° C for 120 minutes. After the development, the system was washed well with water and finally treated with ethanol.

The performance of the catalysts obtained in this example was determined through methanation reaction experiments. The experiment was carried out by securing the opposite ends of each tubular catalyst to a tube support and causing a temperature controlling gas to flow within the tube. Reaction gas was supplied from one end of the shell, and the product gas was taken out from the other end. The composition of sampled produced gas was analyzed through gas chromatography. The conditions for the methanation reaction were as follows:

Composition of the reaction gas: 8% CO + 25% $H_2$ + 67% $H_2O$ ($H_2O$ was added to restrict the reaction temperature.)
Reaction temperature: 300° C (at the gas inlet)
Reaction pressure: 30 atm.
Reaction gas supply rate: 240 N l/h.

Prior to the reaction, the oxidized catalyst layer was reduced by causing hydrogen to flow into the reaction system at 500° C for 2 hours. Then, by subsequently introducing the reaction gas into the reaction system the temperature of the reactor increased due to heat of the methanation reaction to obtain a temperature of roughly 480° to 520° C over the entire length of the reaction tube.

The product gas has dehydrated prior to the analysis through gas chromatography. The right hand end column in Table 1 shows the content of methane gas in percent. For the sake of reference, the product gas in case of sample No. 3 had a composition consisting of 37% $CH_4$, 51% $H_2$, 1% CO and 11% $CO_2$. This composition was nearly the theoretical equilibrium composition at 500° C.

EXAMPLE 2.

Carbon steel tubes 12 millimeters in inner diameter, having been degreased, and were descaled by immersing them in 3% hydrochloric acid at 40° C for one minute, followed by neutralization and washing with hot water and then with water at normal temperature. Immediately thereafter, they were put into a chemical nickel plating bath. Chemical nickel plating liquid was forcibly supplied into the tube from one end thereof to enhance the uniformity of the thickness of the plating film on the inner surface of the tube. The plating liquid used was chiefly composed of 0.2 mol/l of nickel chloride, 0.2 mol/l of sodium hypophosphite and an unknown concentration of complexing agent, and the plating was carried out with pH of 4 and a temperature of 90° to 95° C.

Sample No. 9 was subjected to plating for one hour, and the thickness of the nickel plating film was 16 to 17 microns on both inner and outer surface of the tube.

Sample No. 10 was subjected to plating for 3 hours, and the thickness of the plating film was 50 to 55 microns on the inner surface of the tube and 45 to 50 microns on the outer surface of the tube.

Then, each sample tube was filled with a powdery pack (composed of 20% by weight of 35-mesh aluminum powder, 0.6% by weight of ammonium chloride and 79.5% by weight of weight of 150-mesh alumina powder) and was then closed at the opposite ends with refractory brick covers, and then the atmospheric gas was replaced with argon gas. Then, the system was heated in a resistance wire heating furnace at 900° C for 2 hours.

In this heating treatment, aluminum was diffused into the chemical nickel plating layer while at the time forming an alloyed layer between the nickel plating layer and carbon steel. In this way, a covering with a very high peel-off resistance could be obtained.

For the development of the catalyst layer the system was immersed in an aqueous solution containing 10% by weight of caustic soda (at a temperature ranging from 50° to 100° C) to cause dissolution of aluminum, whereby catalytic activity was imparted to the nickel layer. This catalyst layer, however, was very active and capable of being readily oxidized, so that it had to be stabilized for handling. For the stablization purpose, the reactor tube after the development was dried in nitrogen gas, and then the nickel catalyst layer was slightly oxidized in a nitrogen atmosphere containing 1% oxygen.

Each of these reactor tubes obtained in this way was mounted in a laboratory scale high pressure flow type reaction system for the methanation reaction. The reaction system employed was of the external heating type, and in order to observe the activity of the catalyst layer of the reaction tube according to the invention the reaction tube was adiabatically by winding it with adiabatic material with a thickness of 4 centimeters so that the reaction can proceed adiabatically. At the end of the adiabatic reaction $H_2O$ was added to the reaction gas to suppress an increase in the reaction temperature.

The reaction gas was prepared by adding water to a mixture gas composed of 25% $H_2$ and 75% CO such that the molar ratio of water to mixture gas was 2. The rate of supply of the reaction gas was 40 l/h (in the standard state).

About 50 minutes after causing the reaction gas to flow a reactor tube internal pressure of 30 atm. and at a temperature of 300° C, a substantially constant temperature was reached by the reactor tube. Analysis of the product gas through gas chromatography revealed a composition of 30 to 45% $H_2$, 0.5 to 2% CO, 25 to 35% $CH_4$ and 20 to 40% $CO_2$. The rate of reaction was substantially identically with both the samples Nos. 9 and 10 of the reactor tubes.

EXAMPLE 3

Aluminum was diffused by the pack cementation method under the same conditions as in Example 2 into the inner surface of various tubes 6 to 12 millimeters in inner diameter and having respective compositions listed in Table 2 below.

Table 2

| Sample No. | Chemical composition of tube (unit: % by weight) | | | | | | | | |
|---|---|---|---|---|---|---|---|---|---|
| | C | Si | Cr | Mn | Co | Ni | Cu | Mo | Fe |
| 11 | 0.03 | — | — | — | — | 99.9 | — | — | 0.02 |
| 12 | 0.41 | 1.48 | 24.87 | 1.51 | — | 35.0 | — | — | rest |
| 13 | 0.01 | 1.01 | 20.37 | 0.56 | — | 78.6 | — | — | rest |
| 14 | 0.25 | 0.39 | — | 0.51 | 23.05 | 75.8 | — | — | rest |
| 15 | 0.10 | 0.5 | ~2 | 0.5 | 1.5 | 47.3 | — | 9 | rest |
| 16 | 0.05 | 0.33 | — | 0.64 | — | 66 | 32.4 | — | — |

The tubes formed with the diffusion layer was subject to tensile strength and elongation tests over a temperature range from normal temperature to 800° C by sampling test pieces from the individual tubes.

The developing treatment and measurement of the activity with respect to methanation reaction were carried out after Example 2.

Table 3 below shows the results of tensile strength and elongation tests on test pieces of the base having the superficial diffusion layer, the thickness of the diffusion layer and the content of methane in the methanation reaction product gas.

Table 3

| Sample No. | Tensile strength (kg/mm²)/ Elongation (%) | | | | | Thickness of diffusion layer (μm) | Methane content (%) |
|---|---|---|---|---|---|---|---|
| | 20° C | 200° C | 400° C | 500° C | 800° C | | |
| 11 | 45/23 | 40/23 | 35/20 | 28/17 | 8/9 | 180 | 37 |
| 12 | 54/21 | 50/23 | 45/25 | 42/27 | 24/28 | 150 | 15 |
| 13 | 63/41 | 63/43 | 63/48 | 60/50 | 18/53 | 160 | 30 |
| 14 | 51/21 | 46/23 | 41/22 | 35/20 | 15/19 | 180 | 33 |
| 15 | 80/43 | 75/50 | 71/50 | 68/45 | 38/30 | 150 | 22 |
| 16 | 62/46 | 58/43 | 55/40 | 47/33 | 11/3 | 180 | 32 |

While many cracks were formed in the diffusion layer with the deformation of the test piece during the tensile strength test, the diffusion layer was not separated from the base metal, thus proving excellent peel-off resistance.

In case of sample No. 12 the nickel content in the base material was 35 percent, and the catalytic activity for the methanation reaction was inferior. Nearly the theoretical methane production rate could be obtained if the nickel content was substantially 60 percent or above.

As long as the base material has a tensile strength of 35 kg/mm² or above and an elongation of 20% or above at 500° C, the reactor does not require any reinforcing material so that it is possible to design a reactor of a simplified construction.

EXAMPLE 4.

Figure 3:
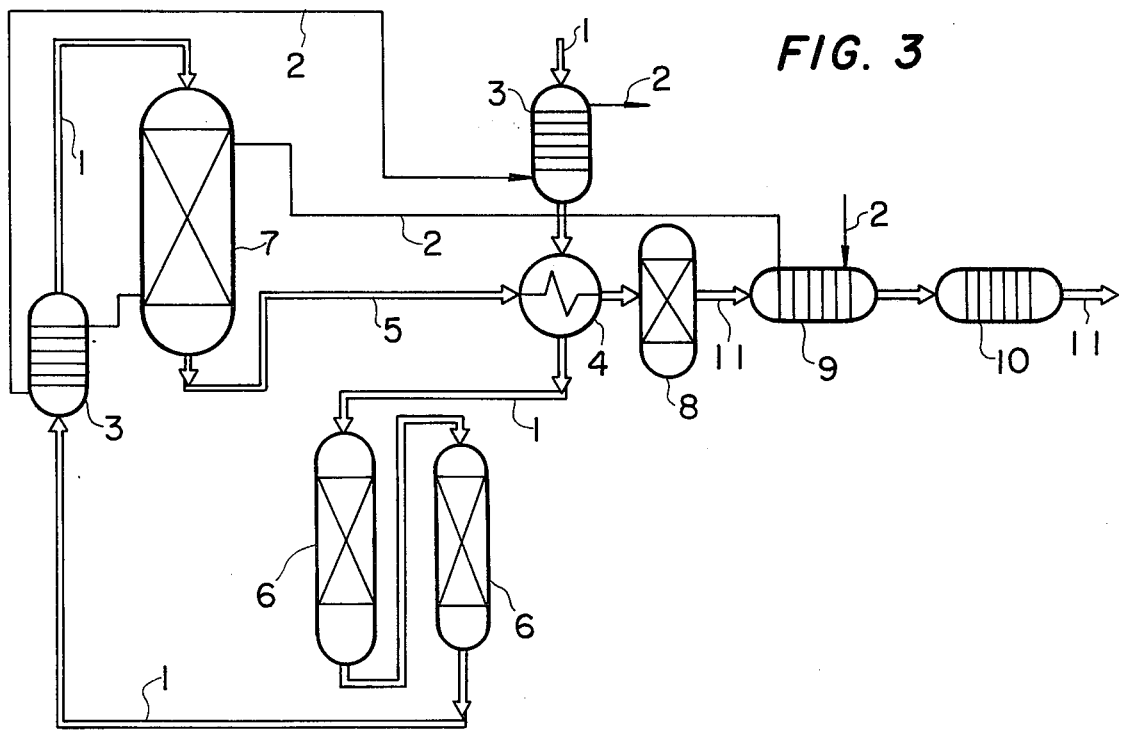
FIG. 3 is a schematic representation of a methanation reaction process system set up as in accordance with the invention, and in which material gas 1 is preheated by cooling medium 2 in waste heat boiler 3, then super heated in super heater 4 by product gas 5 and then passed through purifiers 6, methanation reactor 7, carbon monoxide gas converter 8, cooling medium preheater 9 and cooler 10 to obtain product gas 11.

FIG. 3 shows a processing system as an example of the methanation reaction system according to the invention. The material gas used is, for instance, a mixture gas composed of carbon monoxide gas (CO) obtained through gasification of coal and hydrogen gas obtained through decomposition of naphtha, both these component gases containing sulfur. The material gas 1 is preheated in a waste heat boiler 3 with waste heat of cooling medium 2, and it is then super heated in a material gas over-heater 4 with waste heat of methane rich product gas 5, followed by purification in purifying towers 6. Since the purified material gas 1 is reduced in temperature due to purification, it is heated again in the waste heat boiler 3 before it is supplied to the methanation reactor 7, in which the methanation reaction takes place to produce the methane rich product gas 5. Since the methane rich product gas 5 is a high temperature gas at about 500° C, its temperature is lowered by supplying it to the over-heater 4 for over-heating the material gas 1. Further, since it contains carbon monoxide gas (CO) and is harmful to the human body, it is converted in a carbon monoxide gas converter 8 into the harmless carbon dioxide gas (CO₂) through a reaction represented as $$CO + H_2O \rightarrow CO_2 + H_2,$$

thus obtaining the final product gas 11.

The final methane rich product gas 11 is still at a considerably high temperature, so that its temperature is reduced through a cooling medium preheater 10 and final through a cooler 10 down to about 40° C before it is delivered as the final product gas 11. The supplied cooling medium 2 is preheated in the preheater with the waste heat of the product gas, and then after removing a great deal of heat due to methanation reaction in the methanation reactor 7 it is used for the super heating and preheating in the waste heat boilers 3 and is thus reduced in temperature down to the neighborhood of room temperature.

The methanation reactor 7 used had a construction comprising the tubular reactor of sample 13 in Example 3, having the catalyst formed on the inner tube wall, which was welded to a non-annealed steel tube support such that the cooling gas flowed on the shell side.

As has been shown in the above the methanation reaction furnace according to the invention has an advantage that the heat loss is very small for the heat produced due to the methanation reaction is used for perheating and over-heating of the material gas. Besides, the equipment cost is low since the high pressure zone of the reactor is constituted by the interior of the pipe. Further, the heat exchange capacity of the reactor is so high that nearly the theoretical yield of product gas can be obtained with a single pass of the reaction gas, i.e., without recirculation thereof. Furthermore, since the catalyst layer is carried in the form of a thin film on the metal tube, a preset temperature condition can be reached in a very short time. This means that the start and stop of the system can be controlled readily and quickly.

What is claimed is:

1. A method of producing a methanation reaction catalyst comprising forming an aluminum diffusion layer on the inner surface of a tube of an alloy containing at least 45% by weight nickel and having a tensile strength of at least 35 kg/mm² and an elongation of at least 20% at 500° C. by heating said tube together with a powdery pack comprising an aluminum powder in an amount of 1 to 50 percent by weight, ammonium chloride as an active agent and a heat-resistant inactive carrier for preventing agglomeration of said aluminum powder, said pack being charged into the interior of said tube, and developing said aluminum diffusion layer with an alkaline solution.

2. The method according to claim 1, wherein said inactive carrier is alumina, and said charged tube is heated in a non-oxidizing atmosphere.

3. The method according to claim 2, wherein the powdery pack comprises 40% aluminum, 1% ammonium chloride, and a balance of alumina, said charged tube being heated for 120 minutes at 900° C.

4. The method according to claim 3, wherein the powdery pack comprises 20% aluminum, 1% ammonium chloride, and a balance of alumina, said charged tube being heated for 120 minutes at 900° C.

5. The method according to claim 3, wherein the powdery pack comprises 20% aluminum, 0.5% ammonium chloride, and a balance of alumina, said charged tube being heated for 60 minutes at 800° C.

6. The method according to claim 3, wherein the powdery pack comprises 20% aluminum, 0.5% ammonium chloride, and a balance of alumina, said charged tube being heated for 120 minutes at 600° C.

7. The method according to claim 3, wherein the powdery pack comprises 5% aluminum, 1% ammonium chloride, and a balance of alumina, said charged tube being heated for 120 minutes at 900° C.

8. The method according to claim 3, wherein the powdery pack comprises 5% aluminum, 1% ammonium chloride, and a balance of alumina, said charged tube being heated for 120 minutes at 1,000° C.

9. The method according to claim 3, wherein the powdery pack comprises 1% aluminum, 1% ammonium chloride, and a balance of alumina, said charged tube being heated for 120 minutes at 800° C.

10. The method according to claim 2, wherein the alkaline solution is an aqueous solution of caustic soda at a temperature of from 50° to 80° C.

11. The method according to claim 1, wherein said aluminum diffusion layer has an aluminum to nickel atomic ratio of at least 0.3.

12. A method of producing a methanation reaction catalyst comprising a step of forming an aluminum diffusion layer on the inner surface of a tube containing at least 45% by weight of nickel and exhibiting a tensile strength of not less than 35 kg/mm² and an elongation of not less than 20 percent at 500° C., by heating said tube together with a powdery pack comprising 1 to 50 percent by weight of aluminum, an aluminum oxide as an inactive component and ammonium chloride as an active component, said powdery pack being charged into the interior of said tube, a step of developing said aluminum diffusion layer with an alkaline solution to form an active catalyst layer of 1 to 500 microns thickness, and a step of oxidizing the surface of said active catalyst layer in a nitrogen atmosphere containing oxygen whereby the oxidized surface of the active catalyst layer is easily reduced in an operating atmosphere.

* * * * *